(12) United States Patent
Honkonen et al.

(10) Patent No.: US 7,949,163 B2
(45) Date of Patent: May 24, 2011

(54) METHOD OF EVALUATING PERFORMANCE CHARACTERISTICS OF ARTICLES

(75) Inventors: Robert Stephen Honkonen, West Chester, OH (US); David John Maltbie, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 958 days.

(21) Appl. No.: 11/890,835

(22) Filed: Aug. 8, 2007

(65) Prior Publication Data

US 2008/0034849 A1    Feb. 14, 2008

Related U.S. Application Data

(60) Provisional application No. 60/836,299, filed on Aug. 8, 2006.

(51) Int. Cl.
    *G06K 9/00* (2006.01)
(52) U.S. Cl. ............................. 382/128; 382/132; 73/73
(58) Field of Classification Search .................. 382/128, 382/131, 132
    See application file for complete search history.

(56) References Cited

U.S. PATENT DOCUMENTS

| | | |
|---|---|---|
| 5,171,302 A | 12/1992 | Buell |
| 6,446,495 B1 * | 9/2002 | Herrlein et al. .................. 73/73 |
| 6,659,992 B1 | 12/2003 | Schmidt et al. |
| 6,766,817 B2 | 7/2004 | da Silva |
| 6,839,402 B2 * | 1/2005 | Stabe et al. ...................... 378/20 |
| 6,918,404 B2 | 7/2005 | da Silva |
| 7,066,586 B2 | 6/2006 | da Silva |
| 7,174,774 B2 * | 2/2007 | Pawar et al. ....................... 73/73 |
| 7,549,866 B2 * | 6/2009 | Cohen et al. .................. 434/267 |
| 7,712,640 B2 * | 5/2010 | Honer et al. .................... 223/66 |

FOREIGN PATENT DOCUMENTS

| | | |
|---|---|---|
| WO | WO 96/12459 A2 | 5/1996 |
| WO | WO 2007/146152 A2 | 12/2007 |

OTHER PUBLICATIONS

Siegfried Stapf, Song-I Han, Hardware and Materials, NMR Imaging in Chemical Engineering, 2006, pp. 47-76, Wiley-VCH Verlag GmbH & Co. KGaA, Weinheim.

Siegfried Stapf, Song-I Han, Fluids and Flows, NMR Imaging in Chemical Engineering, 2006, pp. 359-382, Wiley-VCH Verlag GmbH & Co. KGaA, Weinheim.

Siegfried Stapf, Song-I Han, NMR for Food Quality Control, NMR Imaging in Chemical Engineering, 2006, pp. 471-489, Wiley-VCH Verlag GmbH & Co. KGaA, Weinheim.

* cited by examiner

*Primary Examiner* — Tom Y Lu

(74) *Attorney, Agent, or Firm* — Laura L. Whitmer

(57) ABSTRACT

A method of observing a consumer product is provided. The method includes placing a consumer product into an imaging machine, and then using the machine to obtain information regarding the product.

12 Claims, 20 Drawing Sheets

METHOD OF EVALUATING PERFORMANCE CHARACTERISTICS OF ARTICLES

CROSS-REFERENCE TO RELATED APPLICATIONS

This application claims the benefit of U.S. Provisional Application No. 60/836,299, filed on Aug. 8, 2006, which is incorporated herein by reference.

FIELD OF THE INVENTION

This invention relates generally to methods for observing the interior of a consumer product and its packaging, and, more specifically, to observing the interior of a consumer product and its packaging either as manufactured or as used.

BACKGROUND OF THE INVENTION

Observing the interior of various consumer products can provide useful or important information to the product's manufacturer. The manufacturer may want to observe the interior of the product and its constituents or components at any of several stages, including during product design, during manufacture, after the manufacture but before the product is packaged, when the product is in its packaging, upon opening of the package, upon removal of the product from the packaging, when the product is in actual or simulated use conditions, etc.

Further, exemplary but nonexclusive list of entities that may find it desirable to observe the interiors of products and their packaging includes, but is not limited to, manufacturers, competitors, distributors, consumers or consumer groups, quality control organizations, certification organizations, governmental agencies, and so on.

A manufacturer also may desire to observe the interior of many other products and their packaging. For example, a manufacturer may want to observe the interior of various liquids, semisolids, emulsions, and colloids, such as in their packaging. A manufacturer also may desire to observe the interior of any of a variety of products and packaging. Therefore, there is a need in the art for a method of observing the interior of products and their packaging.

SUMMARY OF THE INVENTION

Methods for observing the interior of a consumer product and its packaging, and, more specifically, for observing the interior of a consumer product and its packaging either as manufactured or as used, are provided.

In one embodiment, the invention includes inserting a consumer product into an imaging machine. The imaging machine then is used to obtain information regarding the product.

In a further embodiment, the invention includes placing a consumer product onto a model. The model and consumer product then are placed into an imaging machine. The imaging machine is used to obtain information regarding the fit of consumer product on the model.

In yet another embodiment, the invention includes placing a consumer product into a magnetic resonance imaging (MRI) machine. The MRI machine is used to create at least one slice of information relating to the consumer product.

While multiple embodiments are disclosed herein, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

DETAILED DESCRIPTION OF THE INVENTION

Figure 1:
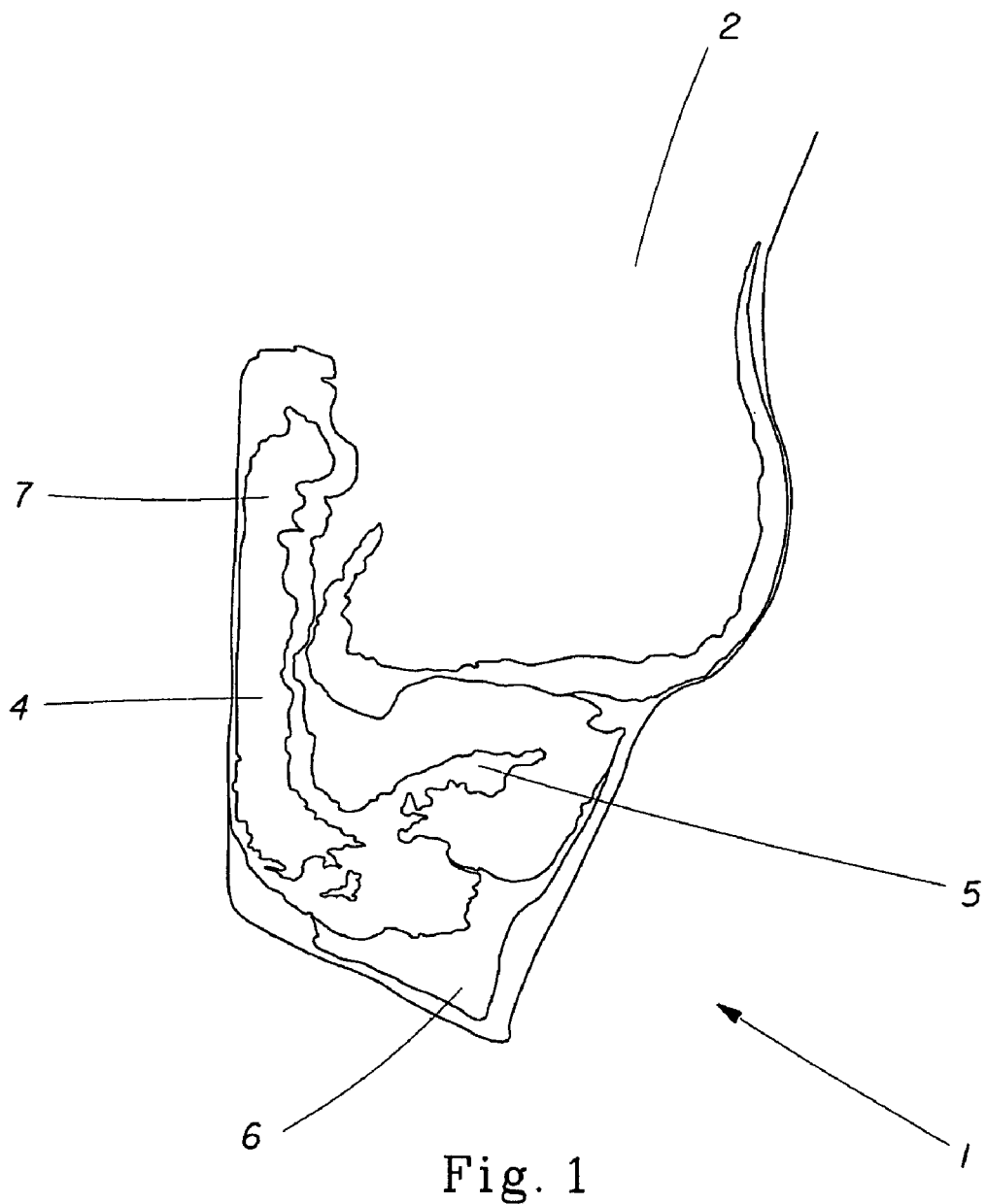
FIG. 1 illustrates information obtained in accordance with one embodiment of the present invention.
Figure 2:
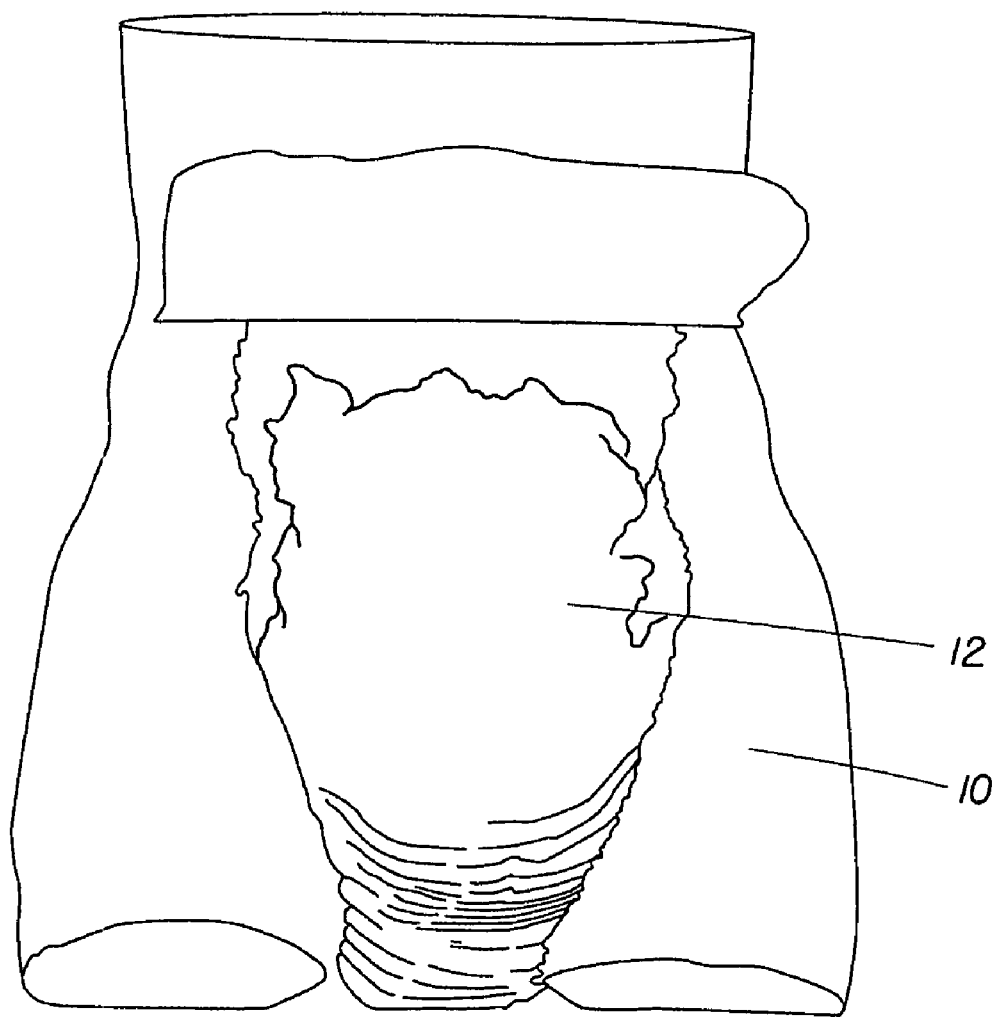
FIG. 2 illustrates an absorbent article on a model based on information obtained in accordance with one embodiment of the present invention.
Figure 3:
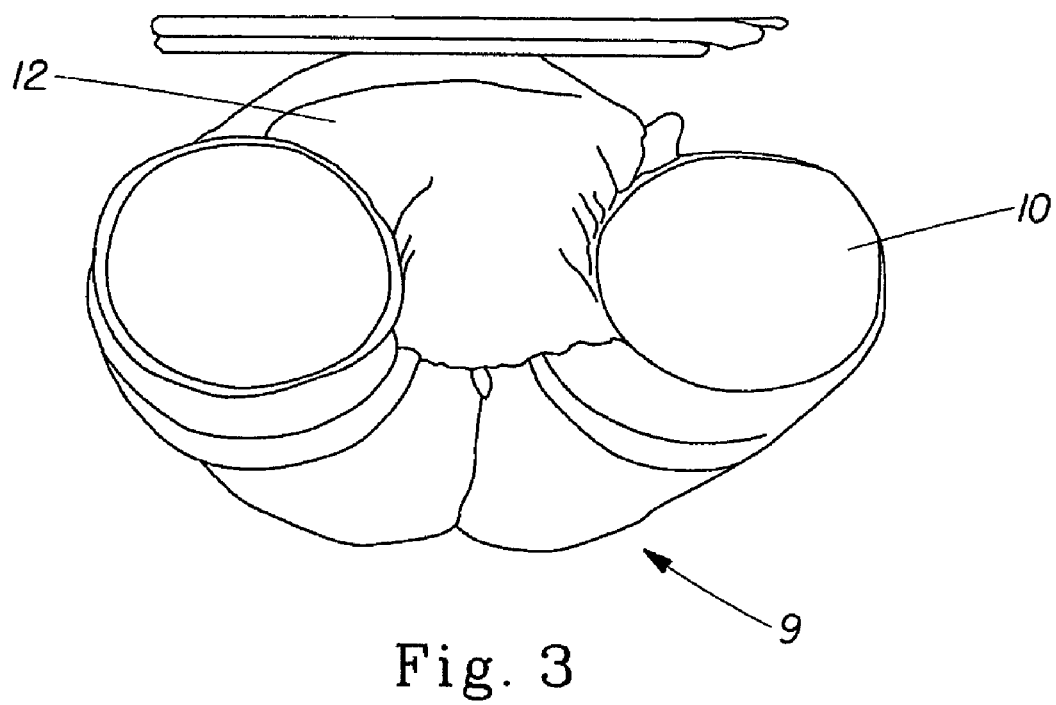
FIG. 3 illustrates the absorbent article on a model of FIG. 2 from a different angle.
Figure 4:
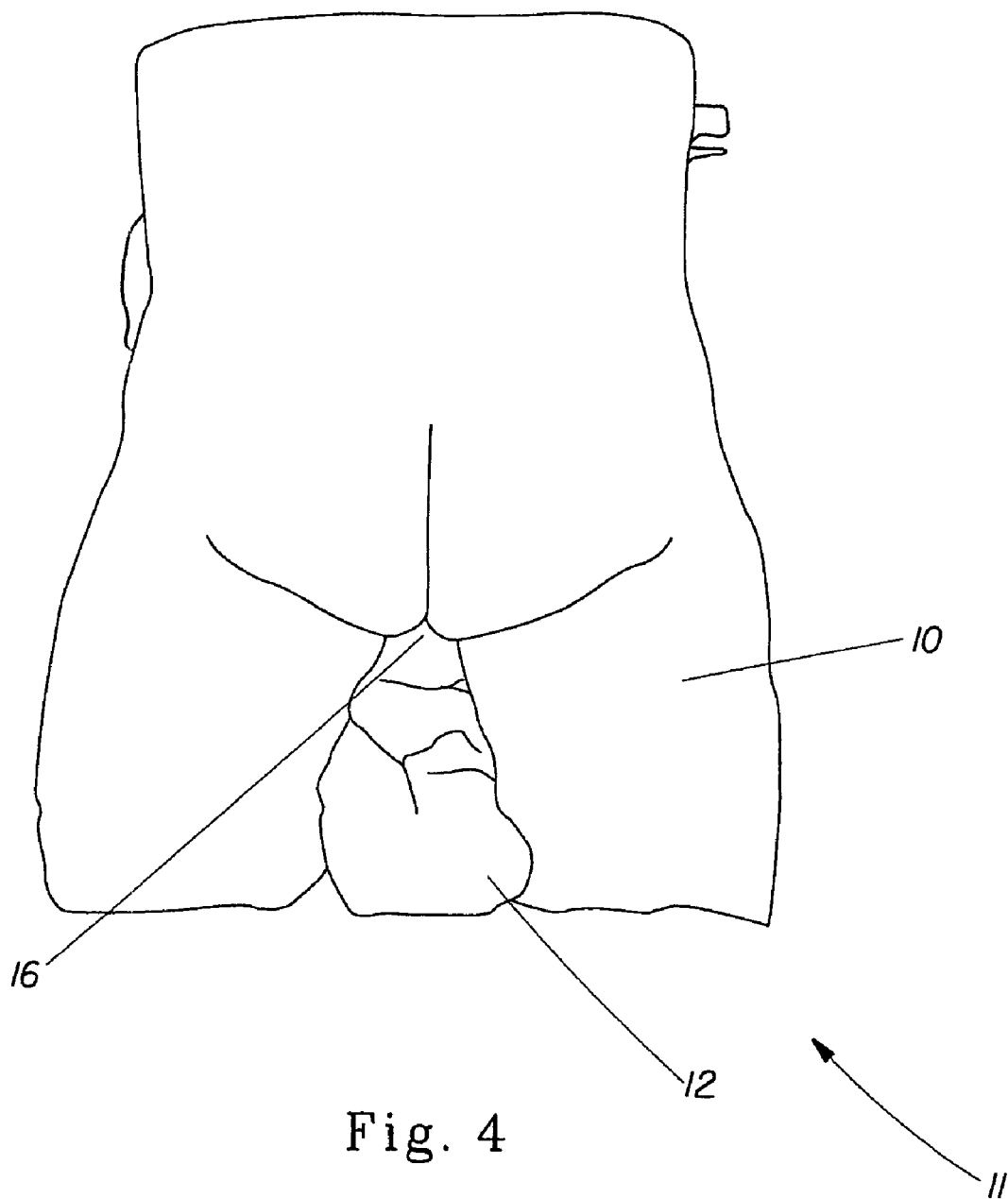
FIG. 4 illustrates the absorbent article on a model of FIG. 2 from a different angle.
Figure 5:
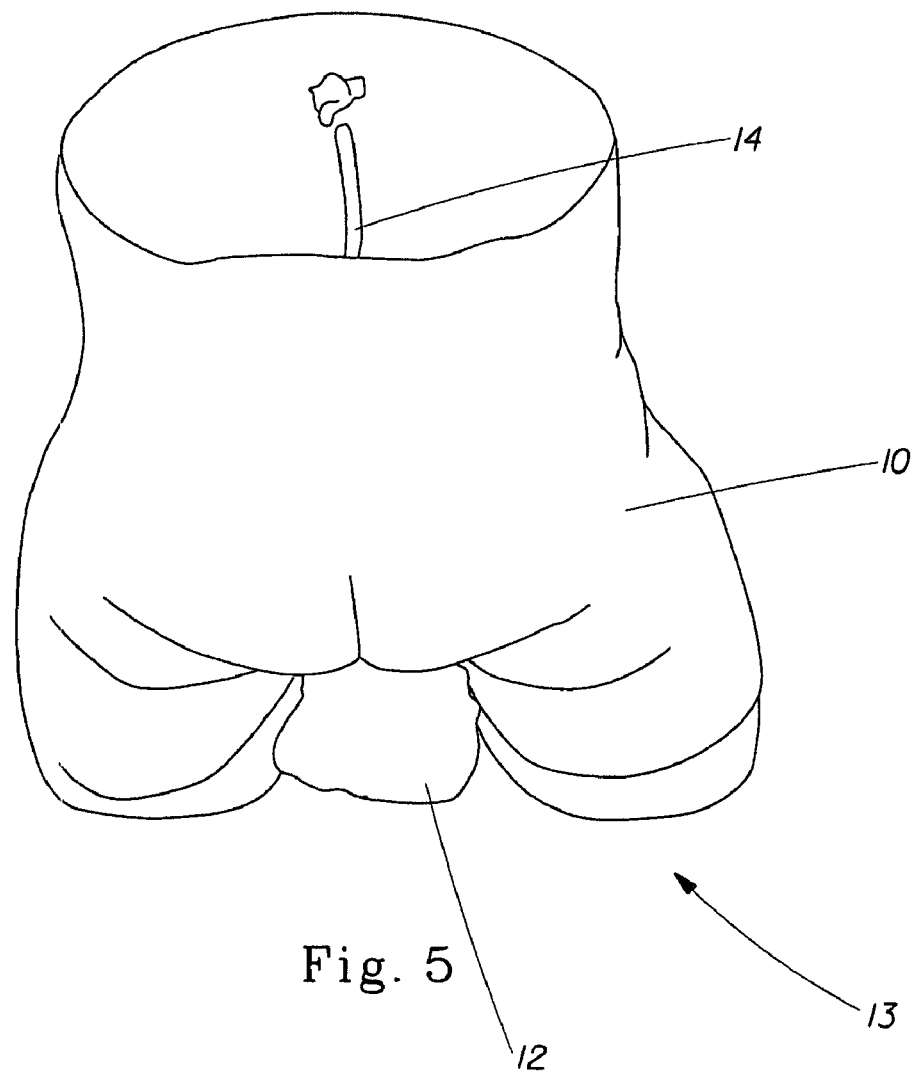
FIG. 5 illustrates the absorbent article on a model of FIG. 2 from a different angle.
Figure 6:
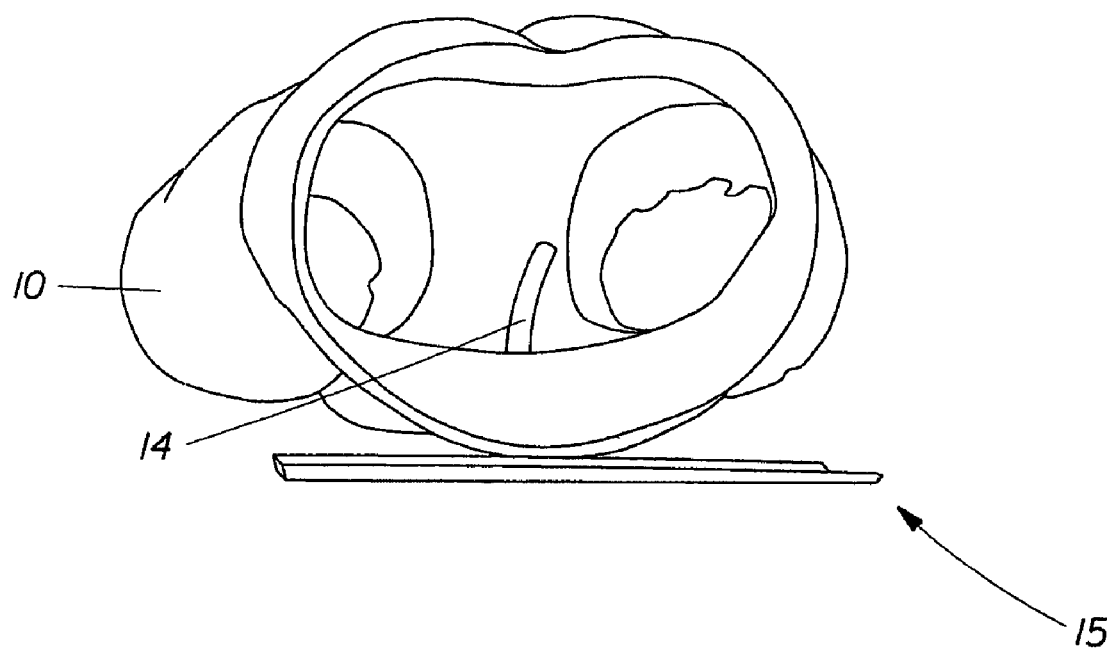
FIG. 6 illustrates the absorbent article on a model of FIG. 2 from a different angle.

Using the scanning and imaging methods of the present invention, it may be desirable for a manufacturer to observe the interior of any of a wide range of consumer products. For example, it may be desirable for a manufacture to observe the interior of any product of interest, such as absorbent articles, cleaning products, batteries, beauty care products, medical products, medical devices, food products, and many other products. Absorbent articles for which a manufacture may want to observe the interior include, for example, bath tissue, paper towels, wipes (e.g., disinfectant, cleansing, facial, hand, baby, perineal), diapers, training pants, catamenial products, wound care dressings, incontinence pads, and bandages. Cleaning products may include absorbent articles and may further include laundry products such as fabric softener sheets and dish care products such as cleaning foam. Beauty care products may include, for example, antiperspirants, toothpaste, skin care products such as lotion, cosmetics such as pressed powders, and hair care products such as hairspray. Medical products and medical devices may include medications, pharmaceuticals, bandages such as athletic bandages or wound care bandages, syrups, salves, etc. Food products may include, for example, snacks such as chips, liquids such as oils, emulsions such as margarine, beverages, etc. The present invention may be used with any suitable consumer product, any portion or constituent of a consumer product, any of the above in packaging, etc.

Observation of the interior of the products and their packaging as disclosed herein can provide a range of useful information, and it can do so in different contexts. For example, it may be desirable for various products to have a range of characteristics. Characteristics that may be relevant to certain products may include, by way of example only, whether the product leaks, shelf life of the product, fit of the product in use, expansion of the product when stored or in use, contraction of the product, package integrity, how the product is distributed in a package, how the product's constituents are distributed in the product or in the package, how the product reacts in a static state, how the product reacts in a dynamic state, how the product reacts while being used, and many other factors that affect the product, its packaging, etc. An examination of the interior of the product or its packaging may provide information regarding one or more of these characteristics.

Moreover, when a product is made, the product may be made pursuant to various quality or control specifications. Examination of the product's interior, or the interior as it relates to the packaging, may be useful for evaluating compliance with such specifications. In some situations, evaluating compliance with specifications may involve intrusive or destructive examination of the product, which may not provide representative or accurate information regarding the product's characteristics. In other situations, evaluating compliance with specifications may involve intrusive or destructive examination of the product's packaging, which again may not provide representative or accurate information regarding the characteristics of the product or its packaging.

Before a manufacturer begins commercial production of a product, the manufacturer may conduct various testing on the product and its packaging. Before manufacturing a product, the products are designed and tested using either a virtual model, an actual physical product, other suitable methods, or combinations of the above. Virtual models are based on assumptions and calculations. They attempt to approximate what a product will do in certain circumstances and environments. Virtual models can be useful when actual physical tests are difficult to perform, hard to generate accurate data, or are generally expensive to conduct. Virtual models, however, can yield information that differs from how the product and its packaging actually perform or react in various environments, which may result in imperfections in products and imperfections in the packaging of products.

A manufacturer also may desire to observe the interior of various products in actual or simulated usage conditions. For purposes of illustration only, one example of a product category whose interior may be of interest to a manufacturer during use conditions is absorbent articles. A manufacturer also may want to observe the interior of many other products and their packaging during use and other conditions. With regard to the example of absorbent articles, exemplary absorbent articles include diapers, incontinence pads, training pants, tampons, and catamenial napkins, paper towels, etc. Some of these examples include an absorbent core that may receive and hold bodily exudates. Any absorbent article with any suitable absorbent core may be used with the present invention.

One characteristic of absorbent articles that may be of interest to a manufacturer is the product's ability to absorb and contain bodily discharges, including initial, subsequent, and continuous or repeated discharges, and the product's ability to contain such discharges without leaking. Another characteristic of absorbent articles that may be of interest to a manufacturer is the actual, as opposed to predicted, flow pattern of liquids as they move through the absorbent article after contacting the absorbent article. The flow path of liquids within the interior of the absorbent article may provide useful information, including but not limited to where the core should have increased absorptive capacity, how to channel liquids away from areas that may be more susceptible to leakage, how to wick and otherwise control fluid flow, etc. Where a given region of an article is more susceptible to leakage, information regarding the actual flow path, including direction, timing, etc., of the liquid to the region in question may aid a manufacturer in improving the product's ability to contain bodily discharges. In general, one reason why an absorbent article may be unable to adequately handle multiple discharges of liquid is the article's limitations regarding transporting discharged liquid away from the region of discharge, once the absorbent capacity of that region has been reached. Thus, the overall performance of the absorbent article may be affected by the article's properties with respect to transporting liquids to the various regions of the absorbent core, including regions that may be located away from the area where the discharged liquids first contact the absorbent core. Other properties relating to the interior of an absorbent article also may be of interest to a manufacturer. For example, information regarding how quickly various absorbent core materials absorb liquids, and how they then transport those liquids, may be helpful in product design and other contexts. In addition, information regarding actual fit—such as how the interior of the article actually contacts and contours the various body configurations—may be helpful in product design, manufacturing, marketing, and other contexts. Indeed, product fit may be of increased importance to various types of products, and to various types of absorbent articles, when compared to others.

Methods for observing the interior of a consumer product and its packaging, and, more specifically, for observing the interior of a consumer product and its packaging, either as manufactured or as used, are provided. The invention is directed to a method of observing product designs using techniques for obtaining data, such as imaging or scanning techniques. Any suitable imaging or scanning technique may be used with the present invention. Examples of suitable imaging processes include but are not limited to MRI, x-ray, computed tomography (CT) scan, etc.

The method of the present invention provides a means for evaluating performance characteristics of whole in tact articles. Additionally, the method of the present invention provides a means for testing an article in an in use situation.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, such as pads or tampons, breast pads, care mats, bibs, wound dressing products, and the like.

Performance characteristics include fluid handling, e.g. absorbency, fluid path, swelling of absorbent material, leakage, distribution of fluid, fluid management, e.g. retention, storage, capacity, acquisition, characteristics of how fluid goes into an absorbent structure, interaction of materials with an absorbent core, wicking, kinetics of fluid movement, e.g. acquisition rate, etc. Performance characteristics also include fit of the article to a wearer. For example, performance characteristics pertaining to fit may include elastic components and their fit to the body, the behavior of absorbent material when dry/wet, fit of the product chassis on a body structure, e.g. mannequin, anatomical integration of the product with the body structure, article behavior during movement, etc.

MRI machines are generally made of a horizontal tube that runs through a main magnet. The main magnet can be a any suitable magnet. Some examples include a permanent magnet, a superconducting magnet, etc. The main magnet may be in the about 0.5 tesla to about 4.7 tesla range, or any individual number within the range. Again, any suitable magnet may be used with the present invention. An MRI machine also may include gradient magnets, which may be of relatively low strength compared to the main magnet. For example, MRI machines may use three gradient magnets. When a person or object is placed in the tube of the MRI machine, the main magnet immerses the person or object in a stable and intense magnetic field, and the gradient magnets create a variable field. It is to be understood that, while particular variations and principles may be discussed herein with regard to MRI or other scanning techniques, any suitable imaging or scanning technique may be used with the present invention. It should further be understood that, unless otherwise stated, reference to imaging or to an imaging machine includes imaging machines, MRI, x-ray, CT, and any other applicable scanning or imaging technique or machine.

For illustrative purposes only, the method of the present invention can include but is not limited to taking the MRI pictures, and using rapid acquisition with relaxation enhancement (RARE), three-dimensional (3D) visualization using multi-slice multi-echo (MSME), other techniques, or subsets or combinations of the above. RARE is a pulse sequence which can be used to collect two-dimensional (2D) slices that allow a user to observe dynamics in real-time, and is sometimes referred to as turbo spin echo, or TSE, or fast spin echo, also called FSE. RARE is commercially available from Bruker Instruments, Billerica, Mass. MSME is a collection of slices that can be resliced to any plane and rendered as 3D surfaces or volumes.

In the present invention, any of the consumer products, portions or constituents thereof, packaging, etc. identified above may be evaluated by imaging techniques to obtain any information of interest, including but not limited to information relating to fluid distribution and containment, fluid flow and transport, product fit, product performance, packaging integrity, product density distribution, how a product fills its packaging, etc. Certain techniques may be better suited for providing information of interest than others. For example, both the RARE and MSME methods allow for the observation and measurement of fluid/solid path, fluid/solid location, fluid/solid intensity, fluid/solid leakage points, product fit, etc. The information obtained by using the RARE and MSME methods allow for correction, and also may allow for the verification of virtual models. In one embodiment, the entire consumer product is inserted in an MRI machine and is observed using either the RARE or MSME methods. In another embodiment, a model (such as a mannequin) adapted to display (or wear) a whole product is placed in an imaging machine for testing purposes. In one embodiment, the model may be a mannequin adapted to accommodate fluids or solids that come in contact with the product. In other embodiments, a portion of a product, or constituents of a product, may be placed in an imaging machine. In other embodiments, product packaging may be placed into an imaging machine. In other embodiments, a product or a portion or constituent thereof that is inside packaging may be placed inside an imaging machine.

In some embodiments of the present invention, where applicable, the product may be placed on a model so as to obtain information relating to how the product performs or responds under actual product usage conditions. The model may be one that represents, that simulates, etc. conditions for actual product usage. The model may have various features that enable the product to be used in a manner that simulates actual usage with respect to the information of interest. For example, where the product of interest is an absorbent article, such as a diaper, the model may take the form of a frame over which the diaper is positioned, or the model may take the form of a mannequin that represents the applicable anatomical geometry of the product's user. Where a mannequin is used, features that simulate actual product usage may include a tube and artificial orifice, or more than one of each, to enable transport of fluid, solid, or semisolid materials from the inside of the mannequin to the absorbent article, such as in a manner that represents soiling of a diaper by urine, fecal matter, or both.

FIG. 1 illustrates information obtained in accordance with one embodiment of the invention. The information may be in any desired form, including a slice, a data file, a graph, waveform, electronic, etc. In the example of FIG. 1, the information may be obtained by RARE, and displayed as a slice. For illustrative purposes only, the product 6 used in the example of FIG. 1 is an absorbent article, in this case a diaper. In the example of FIG. 1, the product 6 may be placed on a model that, for purpose of illustration only, in this embodiment, is a mannequin 2. The mannequin 2 is represented as the dark region defined by the white outline of the mannequin 2. The model may be oriented in any desired configuration and position. In the example of FIG. 1, the mannequin 2 simulates a baby or child wearing an absorbent article in a prone position. To obtain information regarding actual product performance in this context, the product 6 can be placed on a mannequin 2 in a manner that represents how the article is worn, and the mannequin 2 can then be positioned face down in an imaging machine, such as an MRI machine.

The mannequin 2 of FIG. 1 further comprises a tube 5 that represents an artificial urethra. The tube 5 may be dimensioned, constructed, sized, and positioned to simulate a urethra. To obtain the information depicted in FIG. 1, fluid 4 is dispensed through tube 5 into the core 7. As fluid 4 is inserted into the product 6, the intensity, location, duration of the fluid 4 in a given area, and path of the fluid 4 is observed. In one embodiment, the fluid 4 is observed using real-time 2D slices. The data of the 2D slice may be presented in any desired format. In one embodiment, for example, the 2D slices may be about 256×128 points along x and y axes. In some embodiments, the slices taken can be about 5 cm thick and may cover an area of about 24 cm$^2$. In some embodiments, the slices may be about 1.6 mm to about 24 cm, or any individual number within the range. In some embodiments, the slices can be about 1 cm thick to about 5 cm thick. Three dimensional data sets typically comprise about 100 two dimensional slices which are closely spaced or contiguous. In some embodiments, in three dimensional data sets the slices are 2 mm thick. The 3D slices can be, in some embodiments, about 256 by about 256 points along the x and y axes.

The information may be captured at any desired or suitable interval. For example, in some embodiments, a slice 1 can be collected between about every one second to about every 10 seconds. In some embodiments, a slice 1 is collected about every one second to about every four seconds. In some embodiments, a slice 1 can collected about every 2.4 seconds. In some embodiments, a slice 1 can be collected at any non-zero time point, with other slices collected at any desired spacing or intervals. For products whose relevant characteristics operate over different time frames, the spacing may differ. For example, if one were to evaluate how long various phases in a skin care cream will remain homogenously mixed, it may be useful to capture data at intervals that are measured in hours, days, weeks, etc. In other embodiments, the spacing at which information is captured may vary. For example, where the most of a product's effects are substantially immediate and then taper off, it may be desirable to capture more information during the initial phases of the product's use or operation, and then collect the information less frequently as time goes on.

The information may be obtained over any suitable period of time. The period of time that is suitable will vary based on the product and the context in which it is being evaluated. For example, with an absorbent article, such as a diaper, in some embodiments, about one to about five minutes worth of slices 1 may be collected. In some embodiments, about one to about three minutes worth of slices 1 are collected. In some embodiments, about two minutes worth of slices 1 are collected. Any amount of slices 1 lasting any amount of time can be collected. For evaluation of other products, the period of time over which information is collected is likely to exceed several minutes, and may be up to several hours or longer.

Once collected, the information represented by the collected slices 1 can be used in any suitable fashion. For example, the slices may be played in succession, like a movie, which allows a viewer to observe the intensity, location, path, etc. of the fluid 4 or solid, if used, inserted into product 6. For some products and tests involving such products, a single slice 1 is sufficient to observe the characteristics of interest of the particular product. In other situations, it may be desirable to evaluate information displayed in more than one slice, where the additional slice or slices represent other time points, other locations within the article, or both. Where multiple slices are used in succession, they may depict liquid moving through a given location, they may depict liquid as it moves through the article, or both. The slices may depict the position and path of liquid in the article in three dimensions at any time point, they may show the amount of liquid in any given area as a function of time, they may (including with the use of markers) show the wicking and dispersion of liquids as they contact the article, etc.

The collected information can be used for any of a variety of purposes. As discussed above, the information can be used to monitor fluid flow. This information can help identify materials that provide better performance in terms of liquid absorption and containment, leak prevention, liquid dispersion and wicking, elasticity, etc. This information also can be collected in various model positions. For example, in the case of a diaper, the information enables evaluation of liquid containment as the child is in various positions, as the diaper is fastened or secured in different ways, etc. In the case of liquid containment, the information can be used to identify the location or locations where liquid is escaping from the article, the positions of the child when this occurs, the ways the diaper is attached when this happens, the path that the fluid follows as it moves from the site of deposition to the site of leakage, etc.

The information also is useful for evaluating product fit. For example, where the product is a diaper, fit can be evaluated before, during, and after single or multiple liquid depositions; as the child is in different positions; as the diaper is secured by a caretaker in different ways (tightness, position of tape on landing zone, location on hips, etc.), and subsets and combinations of the above.

FIGS. 2-6 depict information 8, 9, 11, 13, and 15 that is obtained in accordance with other embodiments of the present invention. In the example of FIGS. 2-6, information may be obtained using MSME on an absorbent article—in this example, a diaper—that is positioned on a model. As can be seen, this technique allows the image to be rotated, which provides additional detailed information on fit, liquid containment, and the other characteristics discussed above from any of a variety of angles for any given area or areas of interest. In the example shown in FIGS. 2-6, a product 12 is placed on a mannequin 10 and the mannequin 10 is placed in an imaging machine. Product 12 can be any product and for illustration purposes only product 12 is a diaper. Using the MSME method, data can be resliced to any plane and rendered as 3D surfaces or volumes. As discussed above, any number of slices can be collected for any amount of time. In one embodiment, about 5 to about 200 slices are collected. In another embodiment, about 100 slices are collected. The MSME method allows fluid/solid intensity, fluid solid path, fluid solid location, fluid/solid leakage points, and product fit to be observed.

As can be seen in FIGS. 2-6, the mannequin 10 can be of varying sizes to either simulate an adult or an infant human, male or female. This permits evaluation of different products for different users. The mannequin 10 can be of any desired configuration and geometry to represent any given body size, shape, or composition. The mannequin 10 may have a hollow interior portion, which may be adapted to receive a dispenser 14. Alternatively, the mannequin 10 may comprise a foam disposed in the interior portion. The dispenser 14 can carry either fluid and/or semi-solids to the mannequin 10. The mannequin 10 may comprise more than one dispenser such that both urine and fecal incidents can be simulated. The fluids or semi-solids can exit the dispenser 14 and mannequin 10 through an opening 16 in the mannequin 10. The product 12 is adjacent the opening 16 of the mannequin 10 and is adapted to receive the exited contents of the dispenser 14. The liquids and/or semi-solids can be moved through the mannequin 10 in any desired manner. For example, the rate, quantity, consistency, frequency, etc. of fluid and/or semi-solid flow can be varied to represent any combination of parameters of interest. Doing so can provide information, for example, as to how well the article contains and distributes fluids when worn by a 10 pound boy child who sleeps on his side, or how well an article contains runny fecal material when worn by an incontinent 220 pound adult female, etc.

Figure 7:
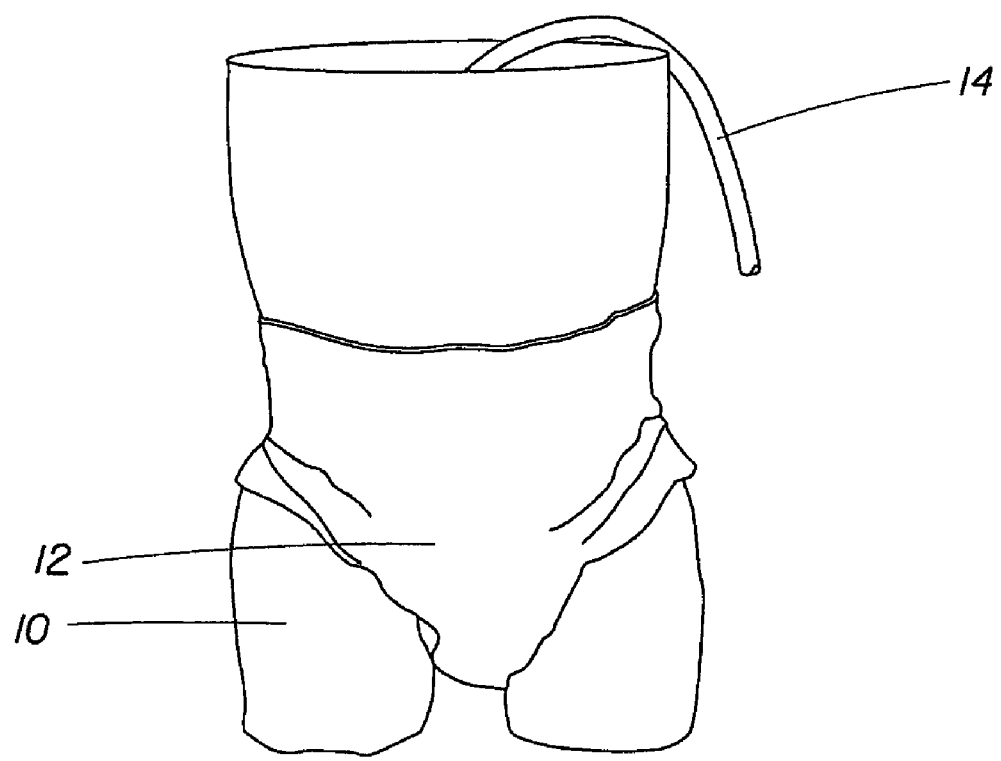
FIG. 7 illustrates a perspective view of a model as used in the embodiments of FIGS. 2 through 6.

FIG. 7 depicts one embodiment of the mannequin 10 and product 12 used to generate the information 8, 9, 11, 13, and 15 shown in FIGS. 2-6. Dispenser 14 can be any desired geometry, and is selected based on the consistency, viscosity, quantity, etc. of the liquid or solid that will travel through it.

Figure 8:
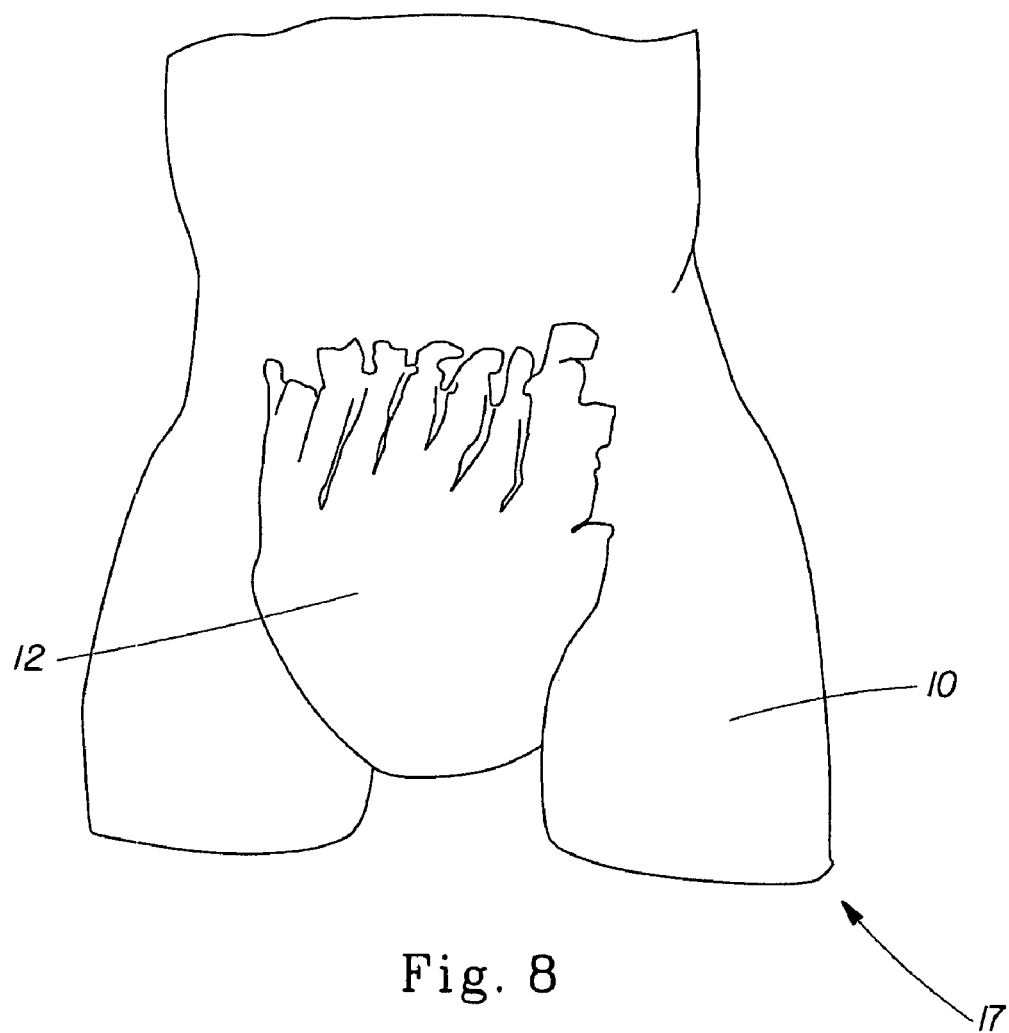
FIG. 8 illustrates information obtained relating to an absorbent article in accordance with another embodiment of the present invention.

FIG. 8 illustrates a 3D surface rendering 17 using an MSME technique on the mannequin 10, as it supports a product 12, as shown in FIG. 7.

Figure 9:
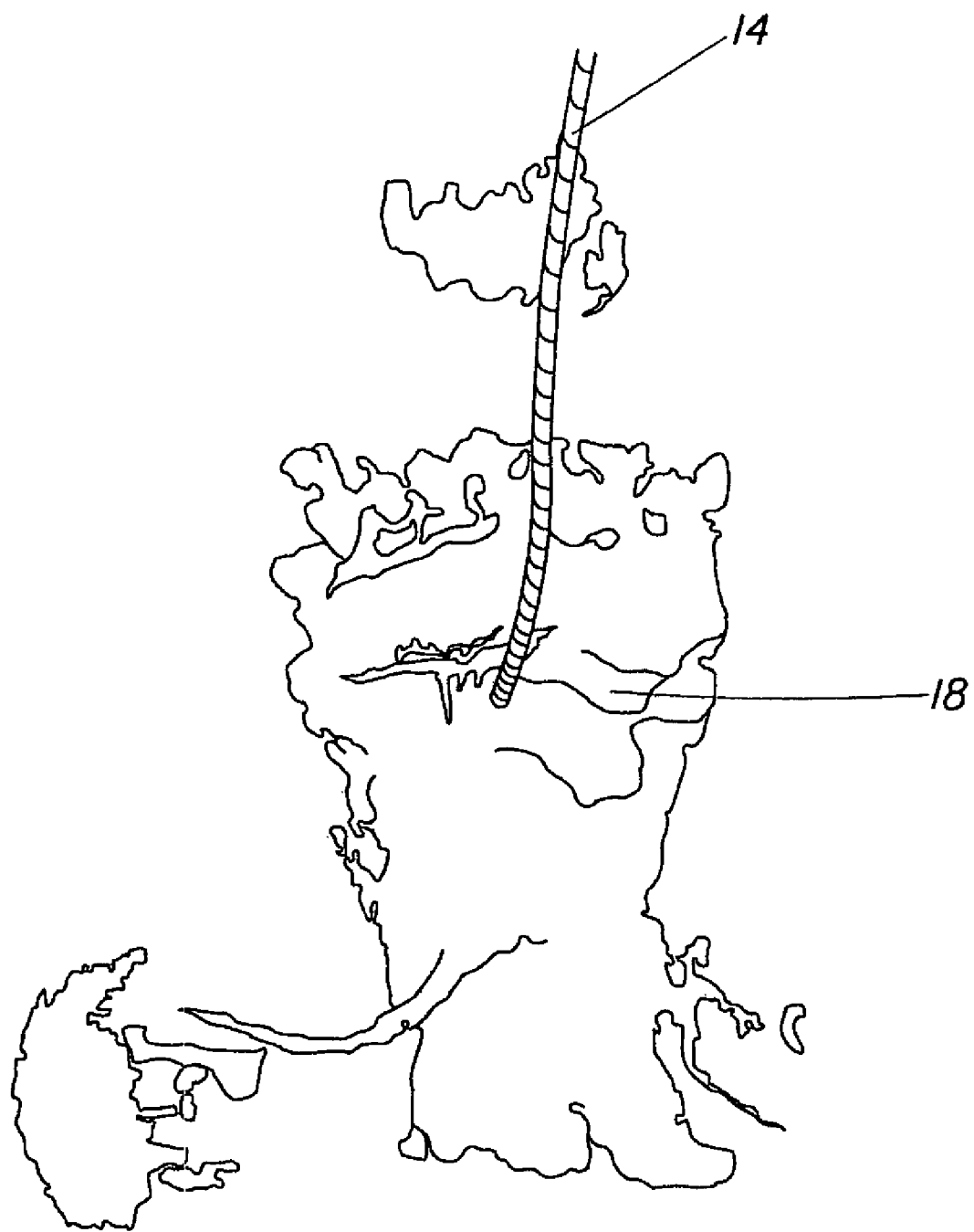
FIG. 9 illustrates information obtained relating to the product core depicted in FIG. 8.

FIG. 9 illustrates another embodiment of the present invention, in which the information is presented as a surface rendering of a swollen product core 18 of the product 12 shown in FIG. 8. In this embodiment, the mannequin 10 shown in FIG. 8 has been filtered out so that it is no longer visible. Any suitable filtering technique can be used to filter out products, mannequins, packages, and other areas that are not of interest in a given test or application. For example, in this embodiment, the fluid exiting the dispenser 14 produces a brighter image than that of the mannequin 10 and dry regions of product 12. By using a brightness threshold, the mannequin 10 may be filtered out leaving only the swollen product core 18 and the dispenser 14. The size, location, and intensity of the swollen product core 18 can be measured and used for virtual modeling purposes. Isolating the swollen product core 18 also provides a manufacturer with information regarding how the core 18 will perform in use condition, how the geometry of the core 18 changes, and how those geometry changes affect fit and how they affect the ability of the core 18 to absorb and distribute subsequent liquid discharges, how the core 18 affects adjacent and surrounding article components as it absorbs fluid and changes geometry, etc.

Figure 10:
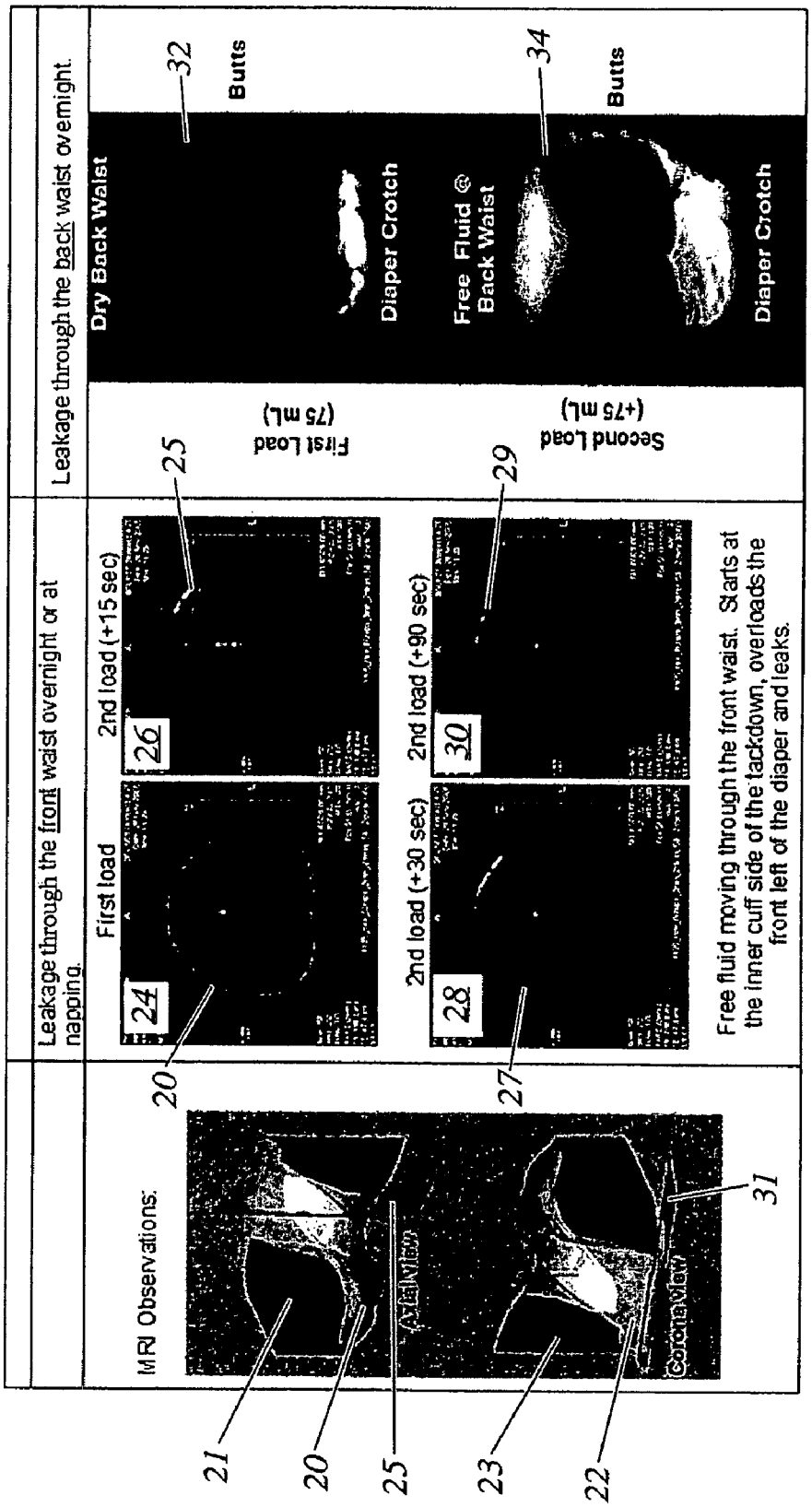
FIG. 10 is another embodiment of the present invention, and depicts observing fluid movement in absorbent articles.

FIG. 10 illustrates another embodiment of the present invention, in which fluid movement may be observed and compared in different products. Any number of different products may be compared, in any relevant aspect. For example, as shown, two products are compared. FIG. 10 illustrates an axial view of a first product 20 on a first mannequin 21 and a corona view of a second product 22 on a second mannequin 23. The first product 20 on the first mannequin 21 is placed in an imaging machine, and, using a suitable technique such as RARE or MSME, a cross-section is taken along plane 25. Slice 24 illustrates the cross-section taken along plane 25 after a first load of fluid has been distributed into the first mannequin 21 and first product 20. The first product 20 is shown to absorb the first load of fluid and no leakage is visible. Slice 26 illustrates the cross-section taken along plane 25 after a second load of fluid has been distributed into the first mannequin 21 and first product 20, and 15 seconds have elapsed. Slice 26 shows an area 25 where some of the fluid is leaking out of the first product 20. Slice 28 illustrates the cross-section taken along plane 25 after a second load of fluid has been distributed into the first mannequin 21 and first product 20, and 30 seconds have elapsed. Slice 28 shows an area 27 where some of the fluid is leaking out of the first product 20. Slice 30 illustrates the cross-section taken along plane 25 after a second load of fluid has been distributed into the first mannequin 21 and first product 20, and 90 seconds have elapsed. Slice 30 shows an area 29 where some of the fluid is leaking out of the first product 20. As shown in slice 30, the amount of liquid (demonstrated by brightness) in area 29 is not as much as in areas 25 and 27. This may be because of the amount of fluid that already has leaked out of first product 20. Slices 26, 28, and 30 demonstrate that first product 20 allows for leakage on the front left side of the first product 20 after a second load is applied. Similar to the first product 20, the second product 22 on the second mannequin 23 is placed in an imaging machine and a cross-section is taken along plane 31. Slice 32 illustrates the cross-section taken along plane 31 after a first load of fluid has been distributed into the second mannequin 23 and second product 22. The second product 22 is shown to have some free fluid in the crotch region with a dry back. Slice 34 illustrates the cross-section taken along plane 31 after a second load of fluid has been distributed into the second mannequin 23 and second product 22. Slice 34 shows that fluid exists in both the crotch region and back regions of the second product 22. The information obtained by this analysis provides guidance on various topics of interest, as described above, including the relationship between size, fit, and positioning on liquid containment, performance of the article's components, etc.

Figure 11:
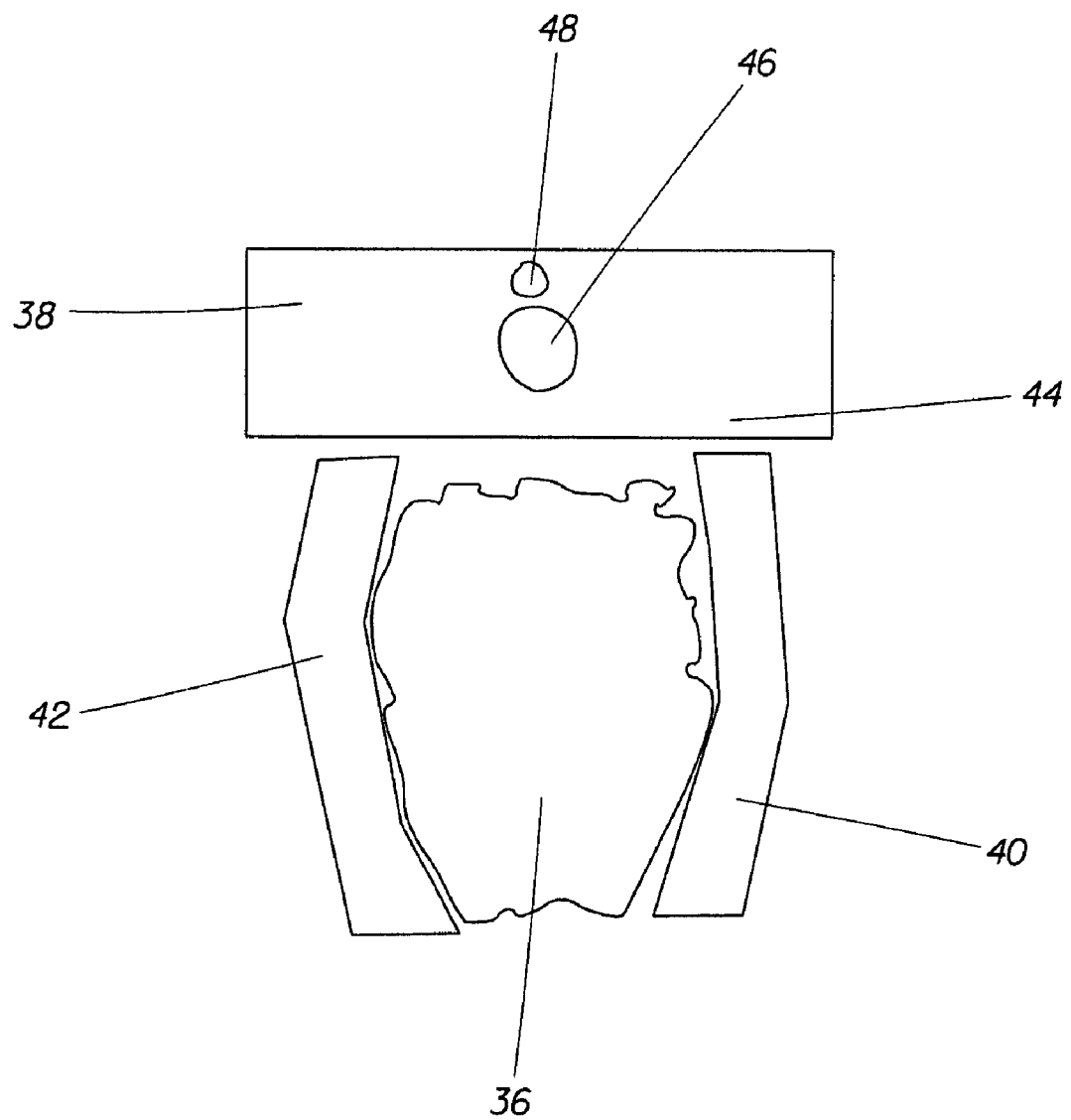
FIG. 11 is one embodiment of defining regions of interest surrounding a portion of interest of a product.

FIG. 11 illustrates another embodiment of the invention, in which defining regions of interests surrounding the core of a product 36 are examined. In FIG. 11, a first region 38, a second region 40, and a third region 42 are defined. Any number of regions can be defined and observed, and the regions can have any suitable shape or size. In this embodiment, product 36 is a diaper with fluid in its core. Product 36 can be any consumer product and can be any shape or size. First region 38 corresponds approximately to the end flap of product 36 and an area of the mannequin holder designed to trap leakage. First region 38 has a marker 44 that corresponds approximately to the bottom of the end flap of product 36. In one embodiment, marker 44 is any substance that is visible by an imaging machine. In another embodiment, marker 44 is an external tube that is filled with a substance that is visible by an imaging machine. When fluid reaches marker 44, fluid has approximately reached the bottom of the end flap of product 36. Within first region 38, a naval marker 48 shows approximately where the naval of the mannequin is located. In this embodiment, fluid has leaked out of the core of the product 36 into the end flap of product 36 and is shown as area 46. Second region 40 corresponds approximately to the right barrier cuff of product 36. Third region 42 corresponds approximately to the left barrier cuff of product 36. If fluid leaks out of the core of product 36, or is about to leak out of the core of product 36 and enters into the first region 38, second region 40, and third regions 42, the fluid is measured and recorded.

Figure 12:
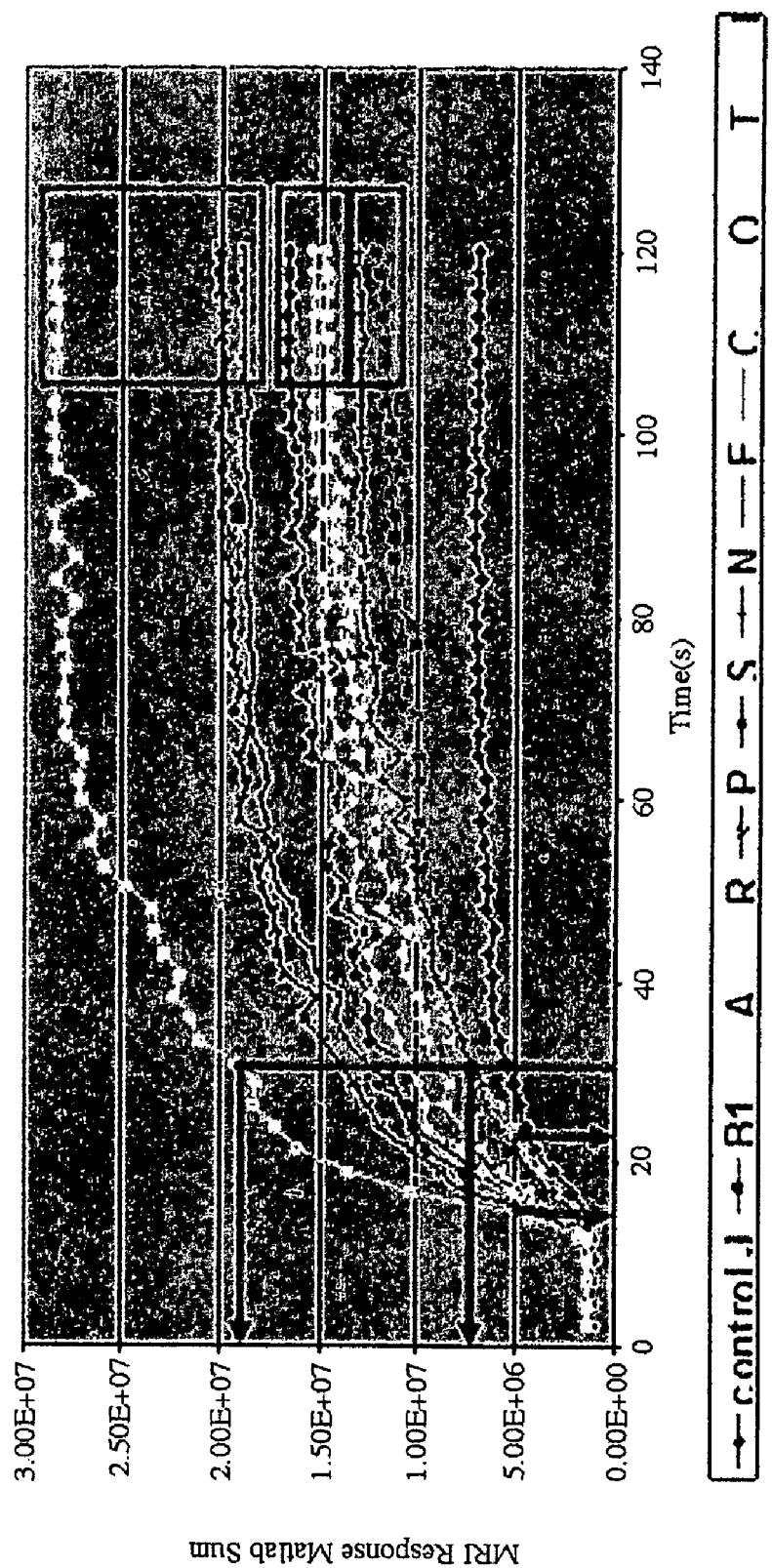
FIG. 12 is one embodiment of quantitative analysis of fluid at one region of FIG. 11.
Figure 13:
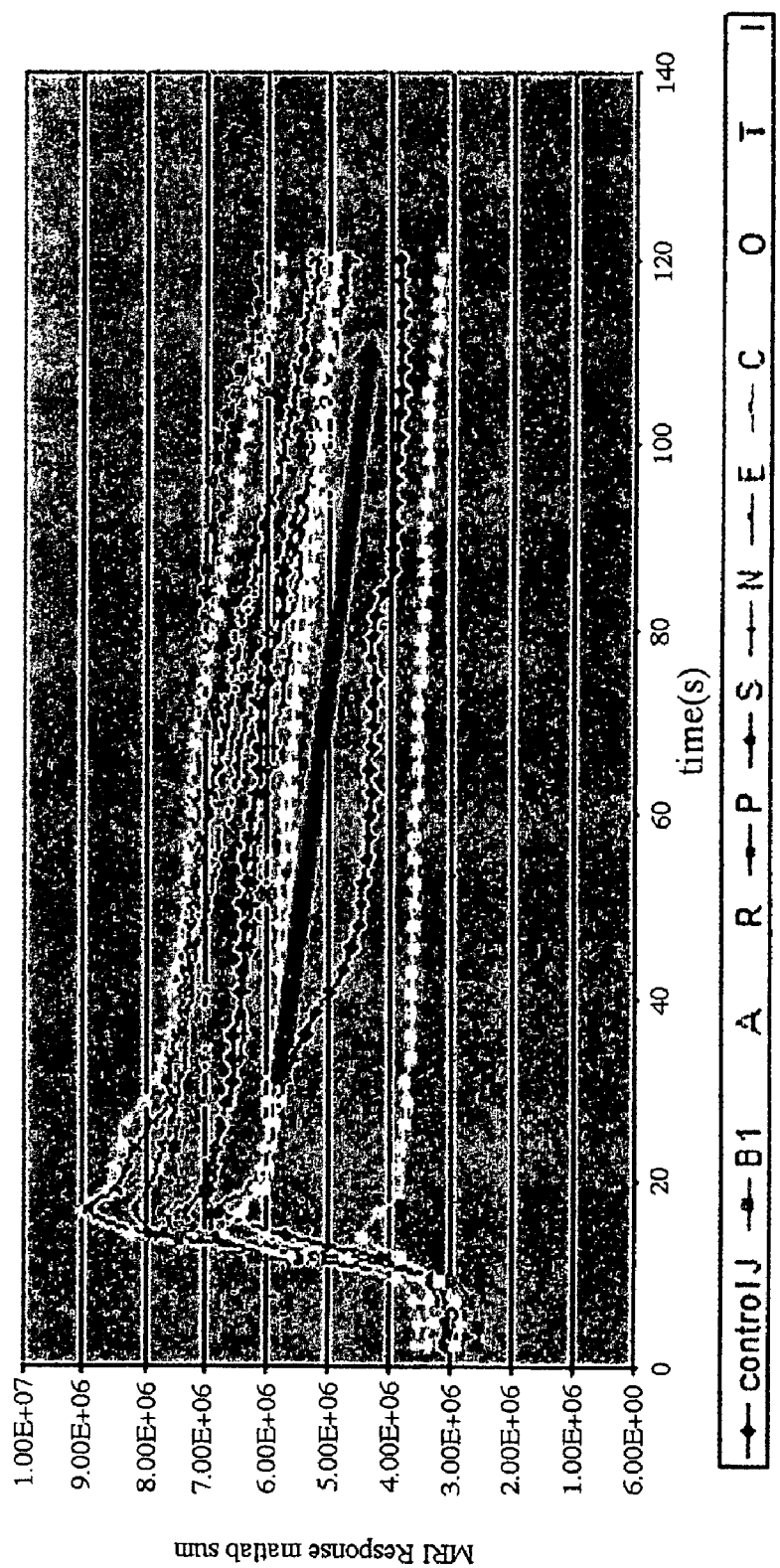
FIG. 13 is one embodiment of quantitative analysis of fluid at another region of FIG. 11.

FIGS. 12 and 13 illustrate further embodiments of the present invention, and show a quantitative analysis of fluid at the first region 38 and third region 42 of FIG. 7. In this embodiment, 12 different products were tested with each product surrounded by an approximately similar first region 38 and third region 42. The intensity of the fluid that entered into each first region 38 for each product was measured and recorded and is shown in FIG. 12. In this embodiment, the intensity measurements correspond to a test using three gushes of fluid and are graphed over a time period of zero to 120 seconds after the third gush, although they may be evaluated with any desired number of depositions of liquid over any suitable period of time. Since first region 38 corresponds to the end flap of a diaper, FIG. 12 approximately illustrates the amount of fluid that leaked out the end flap of a diaper for 12 different diapers. The intensity of the fluid that entered into regions 40 and 42 for each product was measured, summed, and recorded and is shown in FIG. 13. In this embodiment, the intensity measurements correspond to a test using three gushes of fluid and are graphed over a time period of zero to 120 seconds after the third gush. Since third region 42 corresponds to the left barrier cuff of a diaper and 40 corresponds to the right barrier cuff, FIG. 13 approximately illustrates the amount of fluid that leaked out the left barrier cuff and out of the right barrier cuff of a diaper for 12 different diapers.

Figure 14:
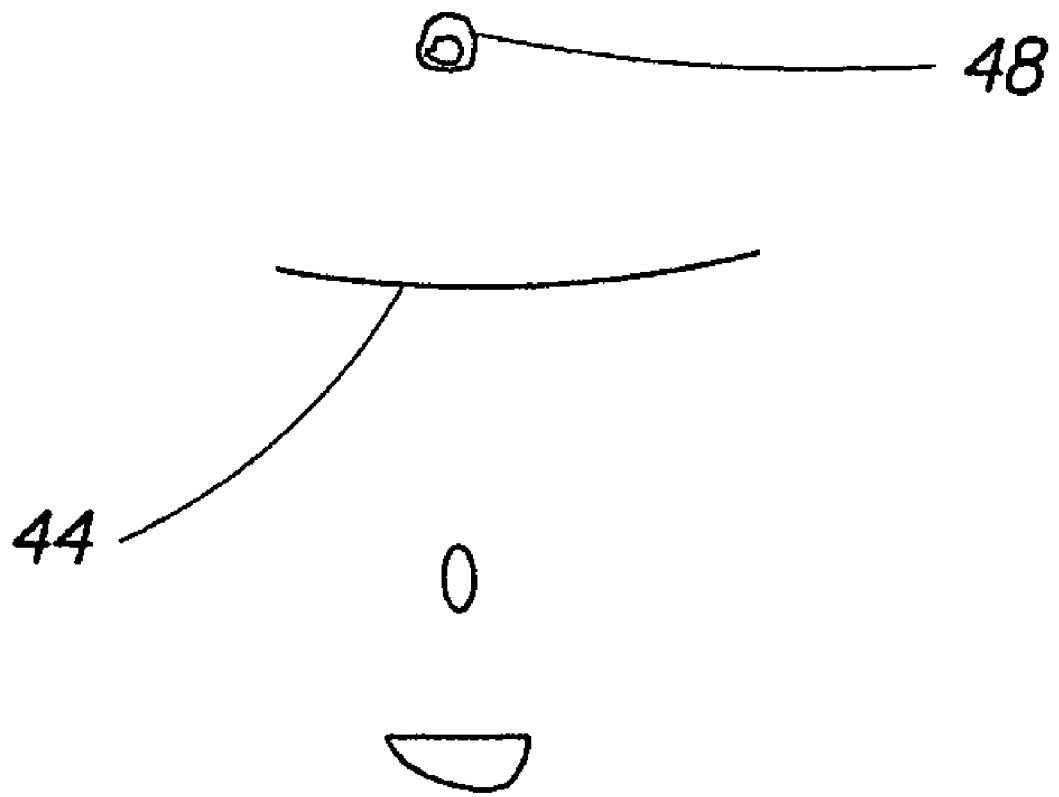
FIG. 14 illustrates information obtained in accordance with one embodiment of the present invention.
Figure 15:
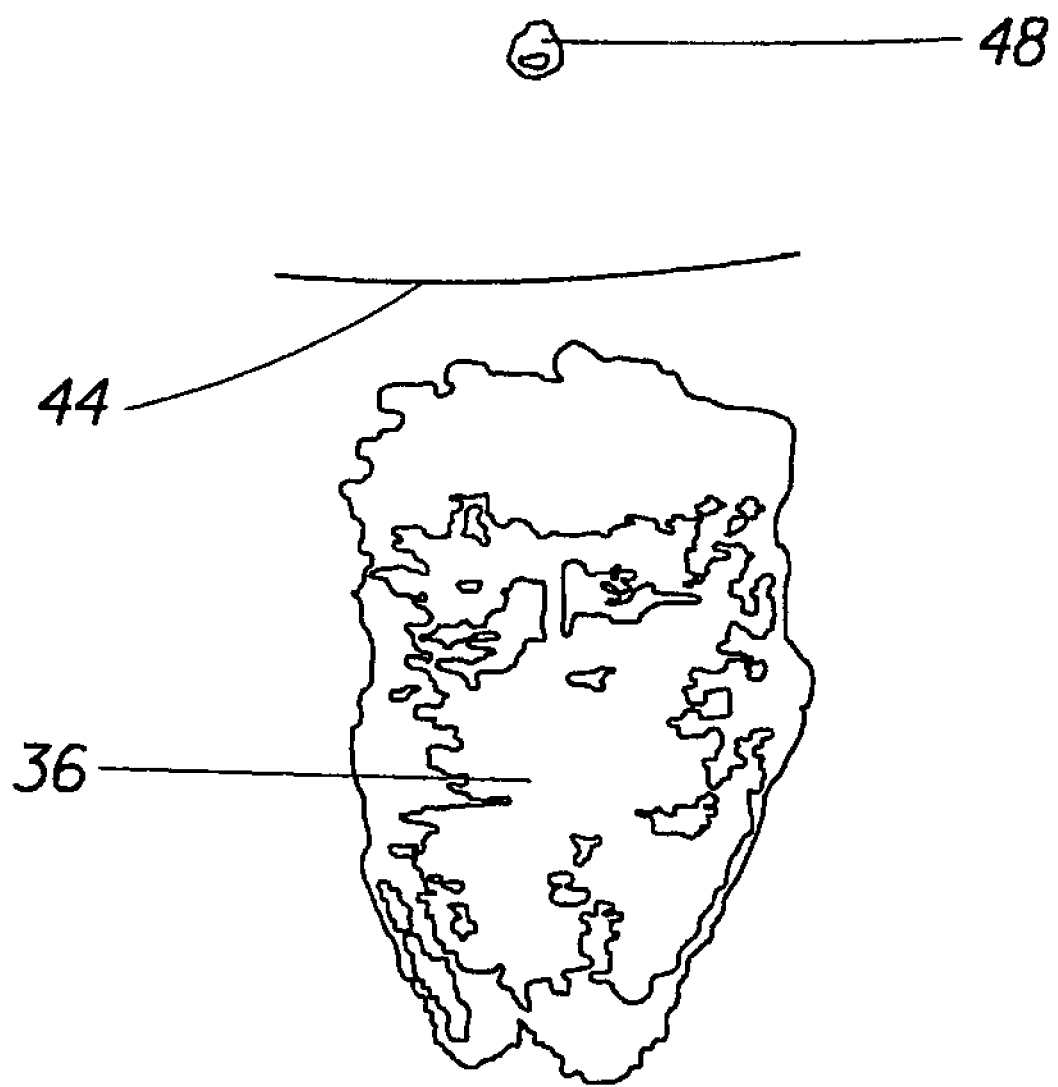
FIG. 15 illustrates information obtained in accordance with one embodiment of the present invention.
Figure 16:
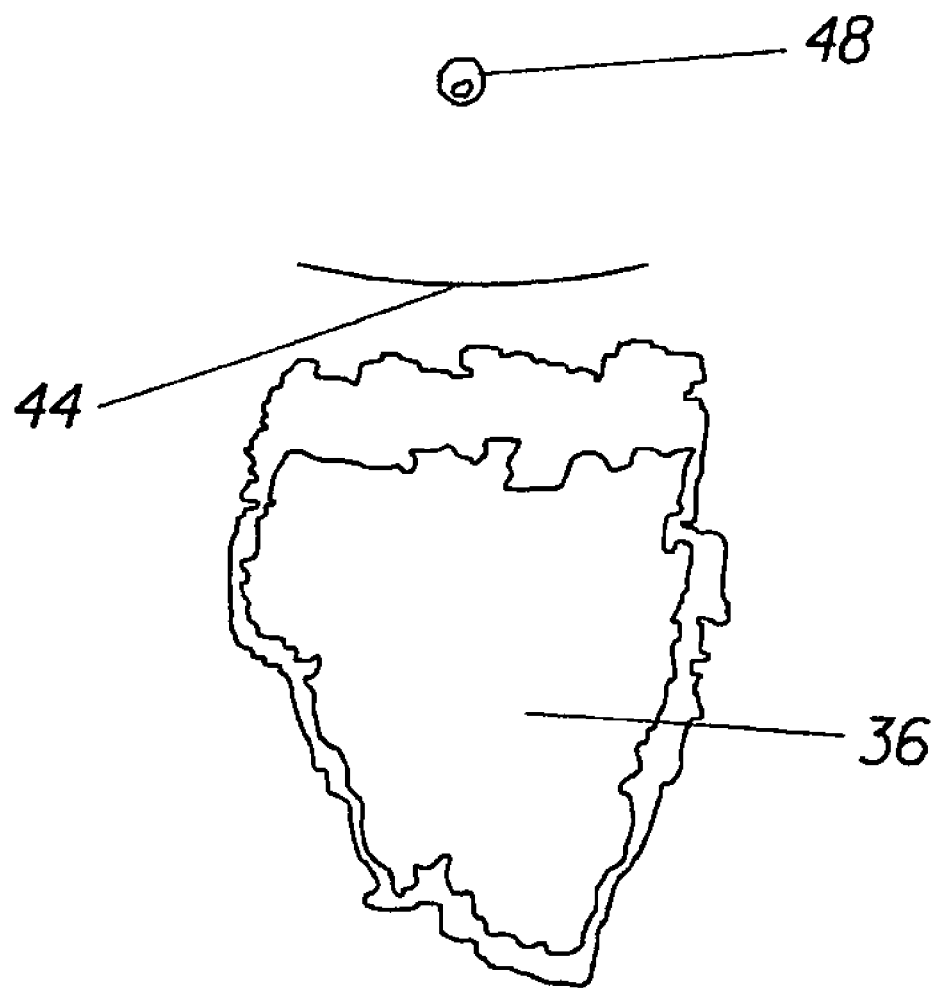
FIG. 16 illustrates information obtained in accordance with one embodiment of the present invention.

FIGS. 14, 15, and 16 illustrate other embodiments of the present invention, in which slices of information are obtained using either the RARE methods. The product shown in FIGS. 14, 15, and 16 can be of any type, shape, or size. In these embodiments, product 36 of FIG. 11 is shown. In FIG. 14, marker 44 and naval marker 48 are visible. The product in FIG. 14 undergoes a first gush of fluid and the intensity of the fluid is measured. In FIG. 15, product 36 undergoes a second gush of fluid. In this slice, the fluid is visible with medium intensity. In FIG. 16, product 36 undergoes a third gush of fluid. In this slice, the fluid is highly visible with high intensity. Also, the fluid in FIG. 16 appears to cover a larger area of product 36 than in FIGS. 14 and 15. This allows for the observance of fluid path, fluid intensity, and fluid location in a product design, along with the other properties described above.

Many materials commonly used for diapers, such as polyethylene and polypropylene, may not be visible using certain imaging techniques, such as MRI. Therefore, in order to visualize product fit, and in this embodiment, diaper chaffing or other product attributes of interest, adjustments to the product may be made. For example, surgical tubing can be filled with a liquid that is visible to an MRI machine. Any suitable liquid may be used. For example, the surgical tubing may be filled with Magnevist doped saline.

Figure 17:
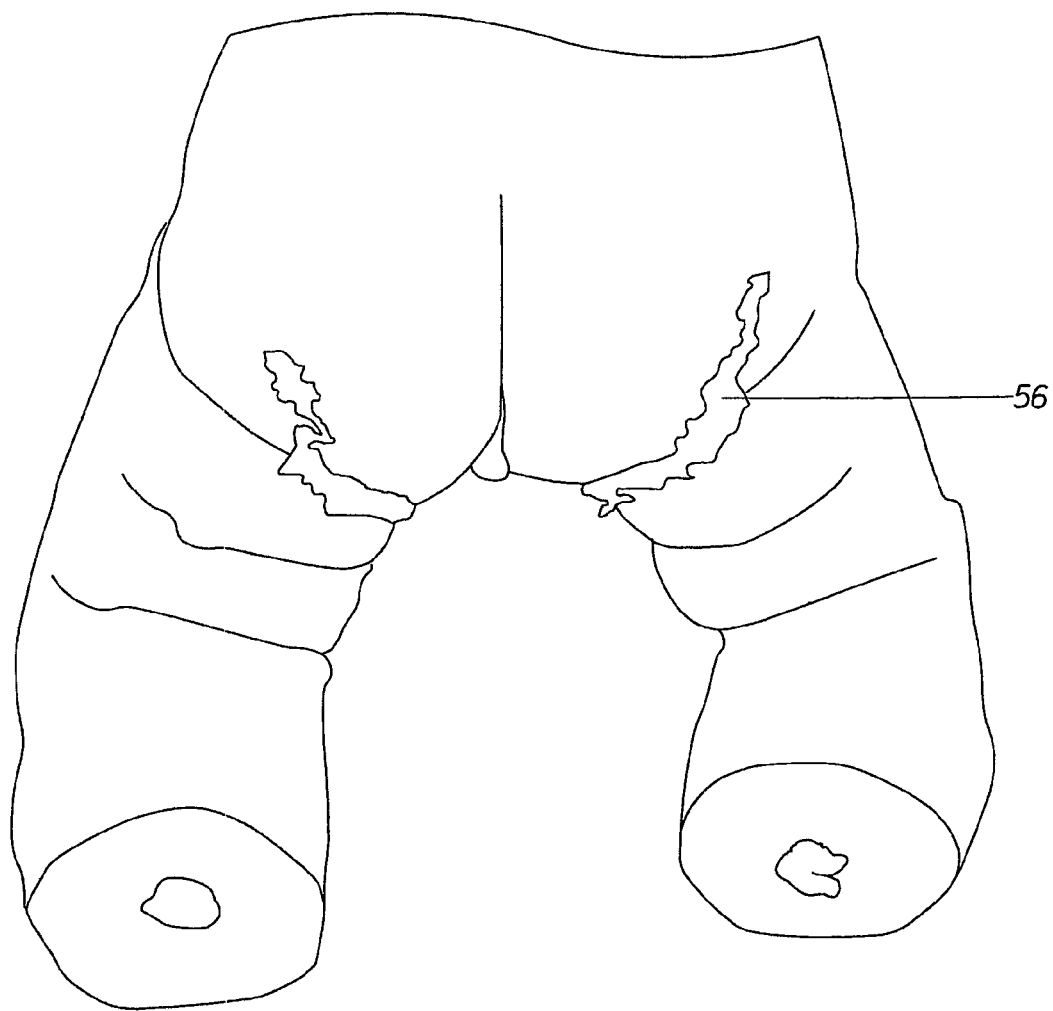
FIG. 17 illustrates information obtained for comparing virtual models to visualized results in accordance with another embodiment the present invention.

FIG. 17 illustrates another embodiment of the present invention, in which virtual models and visualized results may be compared. When testing and designing products, virtual models of the products may be used to estimate the fit, location, and characteristics of the product. Virtual models can at times be inaccurate. In one embodiment cuffs of a diaper can be colored with a substance that is visible to an imaging machine. For example, in one embodiment, the cuffs of the diaper can be colored with polyethylene glycol. In one embodiment, data is retrieved with respect to the location of the cuffs shown by the imaging machine and imported into a software package.

Figure 18:
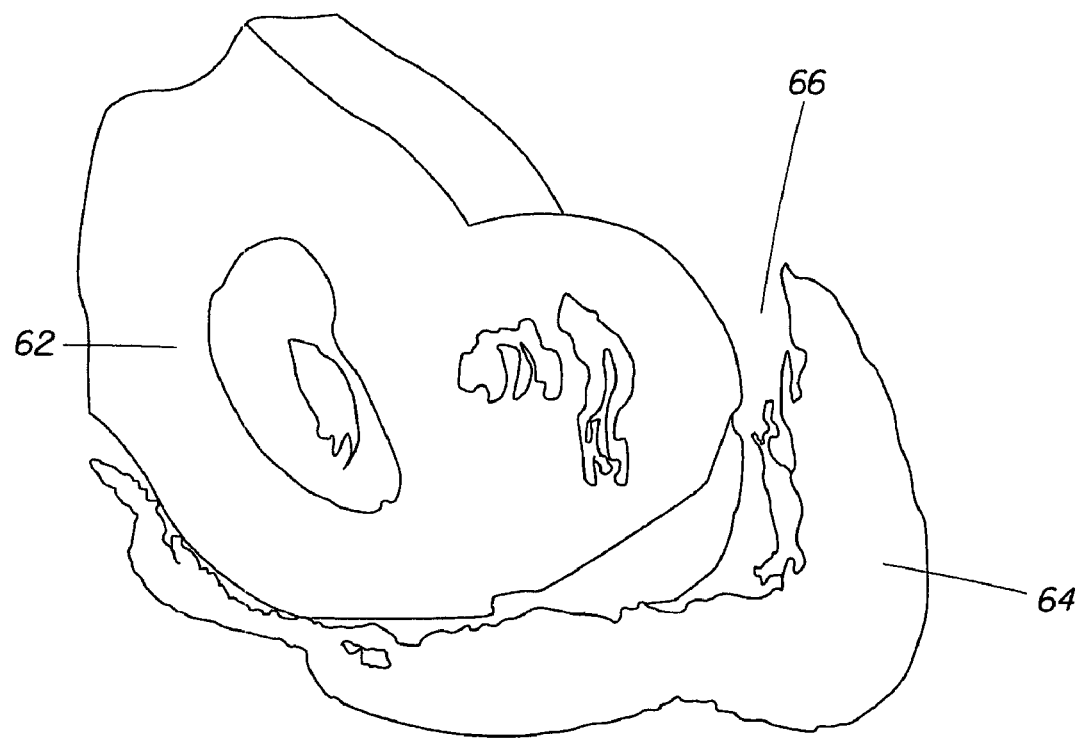
FIG. 18 illustrates information obtained for evaluating product fit in accordance with another embodiment of the present invention.

FIG. 18 illustrates another embodiment of the present invention, in which fit of a product on a mannequin is evaluated. In one embodiment, a product 64 is fit onto a mannequin 62. By using MSME or RARE, a gap 66 between the product 64 and the mannequin 62 is visible and can be measured. The volume of the gap 66 can be extracted and compared to virtual models in order to improve product designs. Additionally, the volume of the gap 66 can be utilized to determine goodness of fit. In one embodiment, a highlighting agent (including but not limited to K-Y Jelly) is used to make the product 64, mannequin 62, or both more visible using the imaging machine. These methods enable evaluation of a product's fit when it first it applied to a user. Where the product 64 is an absorbent article such as a diaper, these methods also enable evaluation of fit as the product is worn, both before, during, and after one or more depositions of fluid or solid material into the article. The methods also enable evaluation of how fit is affected by wear of the article, user movement, deposition into the article of fluids and solids, other conditions, and combinations of these. The information obtained may be used in any of a variety of ways. Where the product 64 is an absorbent article, such as a diaper, the information enhances evaluation of the article's performance, in terms of absorbing fluids, distributing fluids, containing fluids, etc.

The information also may enhance product design. For example, the goal of an article, as for a young baby, may be to keep the child dry and comfortable. In contrast, where the article is intended for use with an older child who may be in the potty training stage, the purpose of the article may be to contain exudates and prevent leaks, while simultaneously maintaining some level of contact between the child and the exudates to prevent the child from being overly comfortable after soiling the article. The techniques of the present invention provide information, such as that based on visual observation, relating to how fluids and solids contact the child as the diaper is worn, which may be useful to the product's designers.

Figure 19:
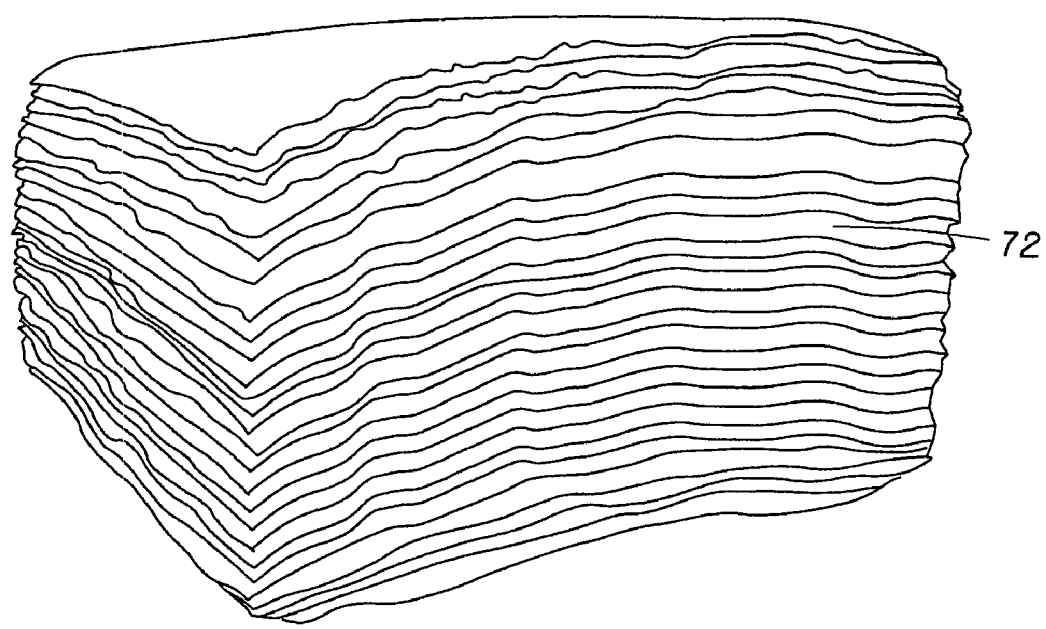
FIG. 19 illustrates information obtained regarding fluid distribution in a packaged product in accordance with another embodiment of the present invention.
Figure 20:
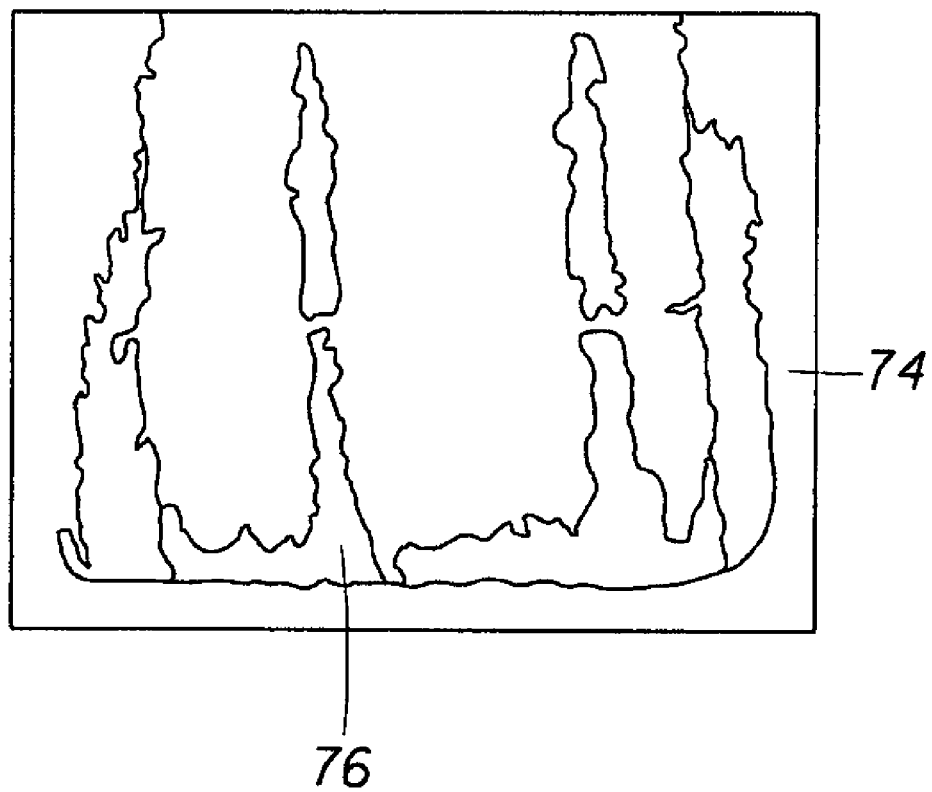
FIG. 20 illustrates information obtained regarding fluid distribution in a packaged product in accordance with another embodiment of the present invention.

While the methods of the present invention have been described in part as they relate to absorbent articles such as diapers, as indicated above and in the following examples, the present invention may be used to obtain information regarding any of a variety of consumer products, product ingredients or constituents, their packaging, etc. For example, FIGS. 19 and 20 illustrate other embodiments of the present invention. FIG. 19 illustrates a product 72, which, for illustrative purposes only, may be a stack of baby wipes. Thus, the present invention may be used to evaluate stacking, compression, etc. of the product inside the packaging, while the packaging remains intact. Moreover, the present invention may be used to evaluate fluid distribution and intensity within the packaging, again without the need to destroy the integrity of the packaging. FIG. 20 illustrates a slice 74 of the product 72 in which the distribution of the fluid 76 is visible. This visualization of fluid distribution within a product, such as product 72 can be measured and extracted and compared to virtual models. It also enables product and packaging designers to evaluate how well the liquids are distributed, including over time, in packaged products where the distribution may be a relevant factor for both manufacturers and consumers.

The present invention also can be used to obtain information that is relevant to determining a product's shelf life. Information relating to any of many consumer products may change over time. For example, it may be desirable for a product to retain certain properties over a known period of time. With respect, for example, to the product 72 of FIGS. 19 and 20, which may be baby wipes, the present invention allows a manufacturer to evaluate the distribution of the fluid within the product, and the retention of the fluid by the packaging, over extended periods of time, without having to disturb the packaging.

Although the invention has been described with reference to embodiments, persons skilled in the art will recognize that changes may be made in form and detail without departing from the spirit and scope of the invention. All directional references (e.g., rear, front, left, right, top, bottom) are only used for identification purposes to aid the reader's understanding of the embodiments of the present invention, and do not create limitations, particularly as to the position, orientation, or use of the invention unless specifically set forth in the claims. It is intended that all matter contained in the above description or shown in the accompanying drawings shall be interpreted as illustrative only and not as limiting. Changes in detail or structure may be made without departing from the spirit of the invention as defined in the appended claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method for evaluating a performance characteristic of an absorbent article for in use conditions, the method comprising the steps of:
   providing a mannequin;
   providing the mannequin with a fluid source;
   placing an absorbent article in fluid communication with the mannequin;
   releasing the fluid source;
   providing an image of the fluid, the absorbent article, and the mannequin with an imaging device; and
   determining the performance characteristic of the absorbent article;
   wherein the imaging device is a magnetic resonance imaging machine.

2. The method of claim 1, wherein a portion of the image is filtered out of a resulting image.

3. The method of claim 2, wherein at least one of fluid intensity, fluid location, and fluid path is observed.

4. The method of claim 1, wherein the performance characteristic pertains to the fit of the absorbent article to the mannequin.

5. A method for evaluating a performance characteristic of an absorbent article for in use conditions, the method comprising the steps of:
   providing a mannequin;
   providing the mannequin with a fluid source;
   placing an absorbent article in fluid communication with the mannequin;
   releasing the fluid source;
   providing an image of at least two components selected from the group consisting of the fluid, the absorbent article, and the mannequin with an imaging device; and
   determining the performance characteristic of the absorbent article;
   further comprising the step of providing an imaging contrast agent to selectively visualize a component of interest.

6. The method of claim 5, wherein the at least two components are the fluid and the absorbent article.

7. The method of claim 5, wherein the at least two components are the fluid and the mannequin.

8. A method for evaluating a performance characteristic of an absorbent article for in use conditions, the method comprising the steps of:
   providing a mannequin;
   providing the mannequin with a fluid source;
   placing an absorbent article in fluid communication with the mannequin;
   releasing the fluid source;
   providing an image of the fluid, the absorbent article, and the mannequin with an imaging device; and
   determining the performance characteristic of the absorbent article;
   wherein the imaging device is an x-ray.

9. A method for evaluating a performance characteristic of an absorbent article for in use conditions, the method comprising the steps of:
   providing a mannequin;
   providing the mannequin with a fluid source;
   placing an absorbent article in fluid communication with the mannequin;
   releasing the fluid source;
   providing an image of the fluid, the absorbent article, and the mannequin with an imaging device; and
   determining the performance characteristic of the absorbent article;
   wherein the imaging device uses at least one of the rapid acquisition with relaxation enhancement and multi-slice multi-echo techniques.

10. A method for evaluating a performance characteristic of an absorbent article for in use conditions, the method comprising the steps of:
    providing a mannequin;
    providing the mannequin with a fluid source;
    placing an absorbent article in fluid communication with the mannequin;
    releasing the fluid source;
    providing an image of at least two components selected from the group consisting of the fluid, the absorbent article, and the mannequin with an imaging device; and
    determining the performance characteristic of the absorbent article;
    further comprising the step of using position markers in the fluid or on the absorbent article or on the mannequin.

11. A method for evaluating a performance characteristic of an absorbent article for in use conditions, the method comprising the steps of:
    providing a mannequin;
    providing the mannequin with a fluid source;
    placing an absorbent article in fluid communication with the mannequin;
    releasing the fluid source;
    providing an image of at least two components selected from the group consisting of the fluid, the absorbent article, and the mannequin with an imaging device; and
    determining the performance characteristic of the absorbent article;
    wherein the imaging device is a magnetic resonance imaging machine.

12. A method for evaluating a performance characteristic of an absorbent article for in use conditions, the method comprising the steps of:
    providing a mannequin;
    providing the mannequin with a fluid source;
    placing an absorbent article in fluid communication with the mannequin;
    releasing the fluid source;
    providing an image of at least two components selected from the group consisting of the fluid, the absorbent article, and the mannequin with an imaging device; and
    determining the performance characteristic of the absorbent article; wherein the imagine device is an x-ray.

* * * * *